United States Patent
Kodera et al.

(10) Patent No.: US 8,399,260 B2
(45) Date of Patent: Mar. 19, 2013

(54) METHOD FOR CONCENTRATION OF LOW-MOLECULAR-WEIGHT PROTEINS AND PEPTIDES IN BODY FLUID SAMPLE

(75) Inventors: Yoshio Kodera, Sagamihara (JP); Tadakazu Maeda, Sagamihara (JP); Yusuke Kawashima, Sagamihara (JP)

(73) Assignee: School Juridical Person Kitasato Institute, Tokyo (JP)

( * ) Notice: Subject to any disclaimer, the term of this patent is extended or adjusted under 35 U.S.C. 154(b) by 0 days.

(21) Appl. No.: 12/672,677

(22) PCT Filed: Aug. 8, 2008

(86) PCT No.: PCT/JP2008/002168
§ 371 (c)(1),
(2), (4) Date: Apr. 6, 2010

(87) PCT Pub. No.: WO2009/019889
PCT Pub. Date: Feb. 12, 2009

(65) Prior Publication Data
US 2011/0177601 A1 Jul. 21, 2011

(30) Foreign Application Priority Data
Aug. 8, 2007 (JP) ................................. 2007-206602

(51) Int. Cl.
*G01N 1/34* (2006.01)

(52) U.S. Cl. ........... 436/177; 436/174; 436/178; 436/86

(58) Field of Classification Search ............... 436/86, 436/174, 177, 178; 530/300, 344, 412, 418, 530/419, 420, 422
See application file for complete search history.

(56) References Cited

FOREIGN PATENT DOCUMENTS
JP 62-65695 3/1987

OTHER PUBLICATIONS

Shen, Chih-Lung et al. "Effect of acid predissolution on fibril size and fibril flexibility of synthetic beta-amyloid peptide." Biophysical Journal (1994) 67 1238-1246.*
International Preliminary Report on Patentability (Chapter II of the Patent Cooperation Treaty) for International Application No. PCT/JP2008/002168, mailed on May 20, 2010 (5 pages).
Jiye A. et al., "Extraction and GC/MS Analysis of the Human Blood Plasma Metabolome", Anal. Chem. 2005, vol. 77, No. 24, pp. 8086-8094 (9 pages).
Hiroshi Okusa et al., "P-277 Nyotampaku Proteome Kaiseki no Tameno Aratana Senryaku", The Japanese Journal of Nephrology, 2006, vol. 48, No. 3, p. 280 (1 page).
Extended European Search Report for European Application No. 08790425, mailed on Dec. 3, 2010 (6 pages).
Kashem et al., "Differential Protein expression in the corpus callosum (splenium) of human alcoholics: A proteomics study", Neurochemistry International, Pergamon Press, Oxford, GB, vol. 50, No. 2, Jan. 17, 2007, pp. 450-459 (10 pages).
Quintana et al., "Identification of chitotriosidase isoforms in plasma of Gaucher disease patients by two dimensional gel electrophoresis", Biochimica et Biophysica ACTA (BBA)—Proteins & Proteomics, Elsevier, vol. 1764, No. 7, Jul. 1, 2006, pp. 1292-1298 (7 pages).
Natarajan et al., "Comparison of protein solubilization methods suitable for proteomic analysis of soybean seed proteins", Analytical Biochemistry, Academic Press Inc, New York, vol. 342, No. 2, Jul. 15, 2005, pp. 214-220 (7 pages).

* cited by examiner

*Primary Examiner* — Yelena G Gakh
*Assistant Examiner* — Christopher A Hixson
(74) *Attorney, Agent, or Firm* — Osha Liang LLP

(57) ABSTRACT

A method for extracting low-molecular-weight proteins/peptides contained in a body fluid sample, particularly, in serum or plasma. The method includes the steps of (a) to (e): (a) adding reagent 1 containing urea and thiourea and reagent 2 containing a reducing agent to the body fluid sample, mixing them, subsequently dropping the mixture into reagent 3 containing 90% or more of an organic solvent, and mixing them; (b) stirring at a low temperature the mixed solution obtained in step (a); (c) centrifuging at a low temperature the stirred solution obtained in step (b) and removing the supernatant; (d) adding reagent 4 containing an organic solvent and an acid to the precipitate obtained in step (c) and mixing them; (e) stirring at a low temperature the mixed solution obtained in step (d); and (f) centrifuging at a low temperature the stirred solution obtained in step (e) and recovering the supernatant.

22 Claims, 10 Drawing Sheets

Evaluation of the method according to the present invention by Tricine-SDS-PAGE (a): SPM 4 μg
(b): Serum 0.5 μl
(c): Mixture of serum 5 μl and SPM 4μg treated by the method of the present invention
(d): Serum 5 μl treated by the method of the present invention
(e): Serum 10 μl treated by the method of the present invention Evaluation of reproducibility of the method of the present invention (1) to (6): identical serum 10 μl treated by method of the present invention
Numbers in ordinate represent molecular weights of extracted low-molecular-weight proteins, etc.

Identification of major peptides, etc. in extract

Evaluation of ultrafiltration method by Tricine-SDS-PAGE (A1), (B1): SPM 4 μg
(A2), (B2): Serum 0.5 μl
(A3): Mixture of serum 5 μl and SPM 4 μg treated by ultrafiltration method
(A4), (B3): Serum 5 μl treated by ultrafiltration method
(A5), (B4): Serum 10 μl treated by ultrafiltration method
(A6), (B5): Serum 100 μl treated by ultrafiltration method

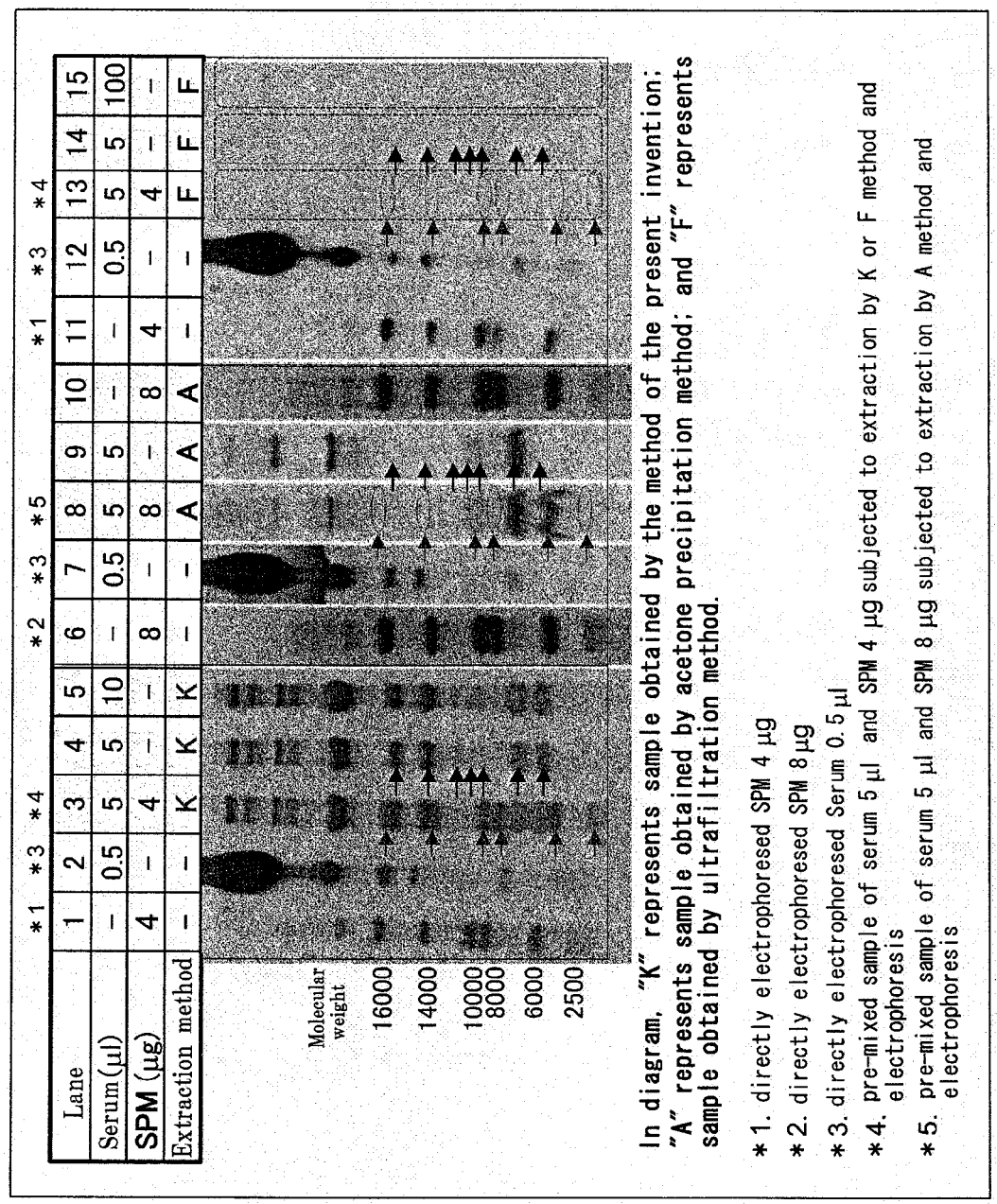

METHOD FOR CONCENTRATION OF LOW-MOLECULAR-WEIGHT PROTEINS AND PEPTIDES IN BODY FLUID SAMPLE

CROSS-REFERENCE TO RELATED APPLICATIONS

This application is a United States national stage application and claims the benefit of PCT application Serial No. PCT/JP2008/002168 filed Aug. 8, 2008, which claims priority to Japanese Patent Application No. 2007-206602 filed Aug. 8, 2007, both of which are incorporated herein by reference in their entirety.

TECHNICAL FIELD

The present invention relates to a method for extracting low-molecular-weight proteins/peptides in a body fluid sample from mammals including humans, particularly, in serum or plasma, and to a kit used for the extraction method.

BACKGROUND ART

In recent years, studies using proteomic approaches have been conducted actively as post-genomic research. This is because proteins as gene products are probably related more directly to the state of disease than genes. Therefore, proteomic analysis is expected to be capable of discovering many pathogenic proteins or disease-related factors undiscoverable by genomic analysis. For example, the proteomic analysis facilitates discovery of biomarker proteins induced or deleted by particular disease. The biomarkers behave in relation to the disease state and as such, highly possibly serve as diagnostic markers or targets for drug development/discovery. Furthermore, the biomarkers lead to the direct interests of patients, such as evaluation of drug responsiveness or prediction of adverse reaction onset.

Recently, matrix-assisted laser desorption ionization time-of-flight mass spectrometers (MALDI-TOF-MS), MS/MS mass spectrometers (tandem mass spectrometers), liquid chromatography mass spectrometers (LC-MS mass spectrometers), and the like have been put to practical use by virtue of the improved performance of mass spectrometers (MS). With such advances of technology, the proteomic analysis has achieved high-speed structural analysis of proteins, etc. as well as high-throughput ultramicroanalysis of polypeptides or identification of previously undetectable, very low-abundance proteins, and has become a strong tool for search for disease-related factors.

However, the proteomic analysis of body fluid samples, particularly serum and plasma, is behind that targeted for biological tissues, in spite of its big clinical advantage. This is because, for example, the abundance of major proteins such as albumin or globulin exceeds approximately 99% of all serum or plasma proteins (Non-Patent document 1), and along with removal of these proteins, the majority of low-molecular-weight proteins/peptides components are also lost.

Pretreatment techniques of removing major proteins in serum or plasma have been developed so far, including: a method comprising obtaining a solution by removing excessive proteins that hamper the detection of low-abundance components (Patent Documents 1 and 2); a method comprising concentrating a fractionated protein solution using a plurality of electrodes (Patent Document 3); and a method for removing major proteins in serum, comprising precipitating large proteins using an organic solvent, and dissociating therefrom low-molecular-weight proteins (Non-Patent Document 2).

However, along with removal of the major proteins, low-molecular-weight proteins/peptides interacting therewith are also lost. Therefore, it has still been demanded to develop a method for concentrating low-molecular-weight proteins/peptides in a body fluid sample, particularly, in serum or plasma, with high efficiency and good reproducibility without being influenced by major proteins.

Patent Document 1: Japanese Patent Laid-Open No. 2005-126376
Patent Document 2: Japanese Patent Laid-Open No. 2005-156249
Patent Document 3: Japanese Patent Laid-Open No. 2007-139759
Non-Patent Document 1: Tirumalai et al., Mol. Cell. Proteomics 2.10, 1096-1103, 2003
Non-Patent Document 2: Merrell et al., Journal of Biomolecular Techniques 15: 238-248, 2004

DISCLOSURE OF THE INVENTION

Problems to be Solved by the Invention

An object of the present invention is to provide a method for extracting low-molecular-weight proteins/peptides in a body fluid sample, particularly, in serum or plasma, with high efficiency and good reproducibility without being influenced by large-abundance proteins, and to provide a kit used for the method.

Means for Solving the Problems

The present inventors have developed a method for searching for disease-related peptides and established a method for extracting peptide components in tissue with high efficiency and good reproducibility. This method comprises two steps and has achieved extraction of 300 to 500 major peptides contained in normal and disease tissues and quantitative comparison using two-dimensional HPLC separation. Consequently, the present inventors have successfully isolated and identified a diabetes-specific peptide present in the renal cortex of diabetes model mice. However, given that the method is applied to human disease, the method, which is targeted for tissue, inflicts large pain or burden on patients during the inspection even if diagnostic markers in the tissue can be discovered. Thus, the method is difficult to actually use. By contrast, if diagnostic markers in a body fluid sample, particularly, in serum or plasma, are discovered, patients can be diagnosed with little pain only by collecting their blood. Furthermore, such diagnostic markers can be applied to medical checkup, highly possibly leading to early detection of disease.

Thus, based on know-how obtained by the establishment of the tissue peptide analysis method, the present inventors have developed a serum-targeted method for extracting low-molecular-weight proteins/peptides. The biggest problem associated with the development of this method is in that the majority of low-molecular-weight proteins/peptides components are lost along with removal of major proteins. This is probably because these low-molecular-weight proteins, etc. are bound with carrier proteins such as albumin or globulin, a major protein in serum. Thus, the present inventors have studied various conditions and consequently, successfully developed a method for extracting low-molecular-weight proteins, etc. in serum or plasma, with high efficiency and good reproducibility without being influenced by carrier proteins.

Thus, the present invention provides a method for extracting low-molecular-weight proteins/peptides contained in a body fluid sample, the method comprising steps (a) to (f) mentioned below:
(a) adding reagent 1 containing urea and thiourea and reagent 2 containing a reducing agent to the body fluid sample, mixing them, subsequently dropping the mixture into reagent 3 containing 90% or more of an organic solvent, and mixing them;
(b) stirring at a low temperature the mixed solution obtained in step (a);
(c) centrifuging at a low temperature the stirred solution obtained in step (b) and removing the supernatant;
(d) adding reagent 4 containing an organic solvent and an acid to the precipitate obtained in step (c) and mixing them;
(e) stirring at a low temperature the mixed solution obtained in step (d); and
(f) centrifuging at a low temperature the stirred solution obtained in step (e) and recovering the supernatant.

The present invention provides the method for extracting low-molecular-weight proteins/peptides contained in a body fluid sample, further comprising the step of (g) lyophilizing the supernatant recovered in step (f).

Moreover, the present invention provides a method for preparing an analysis sample of low-molecular-weight proteins/peptides contained in a body fluid sample, the method comprising adding reagent 5 containing a component to a lyophilized product obtained by the extraction method, the component being selected from the group consisting of TFA, hydrochloric acid, formic acid, acetic acid, and TCA.

Furthermore, the present invention provides a kit for extracting low-molecular-weight proteins/peptides contained in a body fluid sample, the kit comprising reagent 1 containing urea and thiourea, reagent 2 containing a reducing agent, reagent 3 containing 90% or more of an organic solvent, and reagent 4 containing an organic solvent and an acid.
(Definition)

As used herein, the "low-molecular-weight protein" refers to a protein having a molecular weight of 30,000 or less, preferably 20,000 or less. Moreover, the "low-molecular-weight proteins, etc." mean both low-molecular-weight proteins and peptides, unless otherwise specified. Examples thereof include very low-abundance of biologically active proteins (e.g., peptide hormones, interleukins, and cytokines), very low-abundance biomarker proteins having no particular function, and peptides. These proteins or peptides are partially excreted into urine through the kidney. Thus, not only blood but also urine may be used as an analyte in measurement.

As used herein, the "plasma" refers to a supernatant that is obtained by centrifuging blood supplemented with EDTA or heparin or the like and is subject to little or no action of the blood-clotting system.

As used herein, the "serum" is a portion that is obtained by removing clotting components from blood. Fresh blood, when left, is coagulated, and blood cells and fibrin subsequently contract and form a clot, releasing clear amber serum. The serum is almost composed of plasma except for fibrinogen.

As used herein, the "major proteins" and the "carrier proteins" in serum or the like refer to proteins of a relatively large molecular weight contained in serum. Examples thereof include albumin (molecular weight: 66 kDa), immunoglobulin (150 to 190 kDa), transferrin (80 kDa), haptoglobin (>85 kDa), and lipoprotein (several hundreds of kDa).

As used herein, the abbreviation "SDS" means sodium dodecyl sulfate.

As used herein, the abbreviation "PAGE" means polyacrylamide gel electrophoresis.

Effects of the Invention

The present invention can remove proteins of a relatively large molecular weight contained in a body fluid sample, particularly, in serum or plasma, and can extract (or enrich) low-molecular-weight proteins/peptides with efficiency and good reproducibility. Furthermore, the present invention can separate from high-content major proteins (e.g., albumin) middle- to high-molecular-weight (molecular weight: 20,000 to 100,000 or higher) proteins that are not removed by reagents 1 to 4, and can convert these middle- to high-molecular-weight proteins into forms that can be detected and/or quantified by electrophoresis, proteomic analysis, and the like.
(Most Preferable Embodiments for Carrying Out the Invention)

A body fluid sample used for the present invention refers to a solution or the like that is obtained from serum, plasma, urine, saliva, lacrimal fluid, cerebrospinal fluid, ascites, pleural effusion, and various cells of mammals and contains low-molecular-weight proteins and/or peptides. Particularly, the body fluid sample is preferably serum or plasma.

Step (a) of the present invention is the step of adding reagent 1 containing urea and thiourea and reagent 2 containing a reducing agent to the body fluid sample, mixing them, subsequently dropping the mixture into reagent 3 containing 90% or more of an organic solvent, and mixing them.

Reagent 1 has a urea concentration of 1 to 8 mol/l (hereinafter, abbreviated to M), preferably 3 to 8 M, and a thiourea concentration of 0.5 to 3 M, preferably 1 to 3 M. Moreover, reagent 2 contains a reducing agent preferably in such an amount that the concentration of the reducing agent in the mixture of the body fluid sample, reagent 1, and reagent 2 is 1 mM to 20 mM. Thus, reagent 2 contains the reducing agent at a concentration at least 10 to 100 times higher than that in the mixture. For example, the reducing agent concentration is preferably ranged from 10 mM to 200 mM, 10 mM to 1 M, 10 mM to 2 M, or 10 mM to 10 M.

The reducing agent in reagent 2 can be used without particular limitations as long as it can be used in the usual reduction of biological materials such as proteins. Examples thereof include those selected from the group consisting of dithiothreitol (DTT), dithioerythritol (DTE), Tris(2-carboxyethyl)phosphine HCl (TCEP HCl), tri-n-butylphosphine (TBP), 2-mercaptoethanol (2-ME), and mixtures thereof.

When the reducing agent in reagent 2 is dithiothreitol (DTT), dithioerythritol (DTE), 2-mercaptoethanol (2-ME), or 2-mercaptoethanolamine (2-MEA), reagent 2 contains the reducing agent preferably in such an amount that the concentration of the reducing agent in the mixture of the body fluid sample, reagent 1, and reagent 2 becomes 5 mM to 20 mM. Thus, the reducing agent concentration in reagent 2 is 50 mM to 10 M, preferably 50 mM to 1 M, more preferably 50 mM to 100 mM. When the reducing agent in reagent 2 is Tris(2-carboxyethyl)phosphine HCl (TCEP HCl) or tri-n-butylphosphine (TBP), reagent 2 contains the reducing agent preferably in the concentration ranging from 1 mM to 10 mM in the mixture of the body fluid sample, reagent 1, and reagent 2.

Thus, the reducing agent concentration of reagent 2 is 10 mM to 10 M, preferably 10 mM to 1 M, more preferably 10 mM to 200 mM.

Reagent 3 is a solution containing an organic solvent selected from the group consisting of acetone, ethanol, methanol, 2-propanol, acetonitrile, and mixtures thereof, preferably acetone. The organic solvent in reagent 3 has a concentration of usually 90% or higher, preferably 95% or higher, more preferably 98% or higher.

The volume of reagent 3 used in the dropping is at least 10 times or more, preferably 20 times or more, particularly preferably 30 times or more of the mixed solution of the body fluid sample and reagents 1 and 2.

In step (a), proteins and peptides in the liquid sample are treated by the addition of reagents 1 and 2, and the mixture is then dropped into reagent 3 containing 90% or more of an organic solvent that is much higher than an acetone concentration (50 to 70%) in a conventional acetone method or the like. By this procedure, major proteins in the body fluid sample are denatured to break their original structures. On the other hand, even reagent 3 containing 90% or more of the organic solvent causes no or little denaturation of low-molecular-weight proteins/peptides. As a result, the low-molecular-weight proteins, etc. and the high-molecular-weight major proteins are considered to be precipitated in a state that permits easy dissociation therebetween.

Step (b) of the present invention is the step of stirring at a low temperature the mixed solution obtained in step (a).

The low temperature in step (b) is not particularly limited as long as it is a temperature at which components such as proteins in the sample are stable. The low temperature is, for example, −20° C. to 10° C., preferably 0° C. to 5° C. Moreover, the stirring is performed for 1 minute or more, preferably 60 minutes to 120 minutes, more preferably 60 minutes to 90 minutes. Moreover, the stirring can be performed using a stirring machine such as various vortex mixers and stirrers.

Step (c) of the present invention is the step of centrifuging at a low temperature the stirred solution obtained in step (b) and removing the supernatant.

The low temperature in step (c) is not particularly limited as long as it is a temperature at which components such as proteins in the sample are stable. The low temperature is, for example, 0° C. to 10° C., preferably 0° C. to 5° C. The centrifugation is performed under conditions capable of precipitating proteins and peptides in the body fluid sample, for example, at 3000×g to 30000×g, preferably 10000×g to 25000×g, for 1 minute or more, preferably 5 minutes to 30 minutes.

Step (d) of the present invention is the step of adding reagent 4 containing an organic solvent and an acid to the precipitate obtained in step (c) and mixing them.

The organic solvent in reagent 4 is selected from the group consisting of acetonitrile, methanol, ethanol, isopropanol, and mixtures thereof and is preferably acetonitrile. The organic solvent has a concentration of 50 to 99%, preferably 60 to 80%. The acid is selected from the group consisting of hydrochloric acid, TFA, formic acid, acetic acid, and TCA and is preferably hydrochloric acid. Moreover, the concentration of the acid is a concentration at which the major proteins are made poorly soluble by acid denaturation. For example, when hydrochloric acid is used, its concentration is usually 1 mM or higher, preferably 1 mM to 300 mM, preferably 5 mM to 500 mM, more preferably 5 mM to 25 mM. In this context, 0.1 to 500 parts by volume, preferably 1 to 200 parts by volume, more preferably 10 to 100 parts by volume of reagent 4 can be added to one (1) part by volume of the body fluid sample.

Step (e) of the present invention is the step of stirring at a low temperature the mixed solution obtained in step (d).

The low temperature in step (e) is not particularly limited as long as it is a temperature at which components such as proteins in the sample are stable. The low temperature is, for example, −20° C. to 10° C., preferably 0° C. to 5° C. Moreover, the stirring is performed for 1 minute or more, preferably 60 minutes to 120 minutes, more preferably 60 minutes to 90 minutes. Moreover, the stirring can be performed using a stirring machine such as various vortex mixers and stirrers.

The addition of reagent 4 in step (d) and the stirring in step (e) dissolve low-molecular-weight proteins/peptides but not high-content proteins in the body fluid sample, particularly in serum or plasma. This is because reagent 3 containing 90% or more of the organic solvent in step (a) denatures major proteins to break their original structures, whereas the addition of reagent 3 causes no or little denaturation of low-molecular-weight proteins/peptides, as described above. Thus, both these proteins become easily dissociated from each other. Then, the treatment by the addition of reagent 4 dissolves the low-molecular-weight proteins, etc. without dissolving the major proteins and therefore permits separation therebetween. Furthermore, middle- to high-molecular-weight proteins that are not insolubilized by reagents 1 to 4 in steps (a) and (d) are also dissociated from the high-content major proteins and can therefore be analyzed.

Step (f) of the present invention is the step of centrifuging at a low temperature the stirred solution obtained in step (e) and recovering the supernatant.

The low temperature in step (f) is not particularly limited as long as it is a temperature at which components such as proteins in the sample are stable. The low temperature is, for example, 0° C. to 10° C., preferably 0° C. to 5° C. The centrifugation can be performed under conditions capable of precipitating proteins and peptides in the body fluid sample, for example, at 3000×g or more, preferably 10000×g to 25000×g, for 1 minute or more, preferably 5 minutes to 30 minutes.

The supernatant obtained in step (f) is an extract of low-molecular-weight proteins, etc. obtained by the method of the present invention from the body fluid sample. This supernatant can be used directly in proteomic analysis or the like.

Step (g) of the present invention is an additional step and is the step of lyophilizing the supernatant recovered in step (f). By this lyophilization, the low-molecular-weight proteins, etc. from the body fluid sample can be stored stably, while they can be dissolved at a desired concentration in a desired solvent according to analysis methods and subjected to analysis. The lyophilization can be used without particular limitations unless it breaks the low-molecular-weight proteins, etc. extracted in the present invention.

The present invention further provides a method for preparing an analysis sample of low-molecular-weight proteins/peptides contained in a body fluid sample, the method comprising adding reagent 5 containing a component to a lyophilized product obtained by the method, the component being selected from the group consisting of TFA, hydrochloric acid, formic acid, acetic acid, and TCA. Preferably, reagent 5 contains 0.1 to 20% TFA. Alternatively, preferably, reagent 5 contains 0.1 to 20% formic acid, acetic acid, TCA, or mixtures thereof. Reagent 5 can contain various solvents including water, ethanol, methanol, acetonitrile, propanol, acetone, and mixtures thereof. In the preparation method, 0.01 to 100 parts by volume, preferably 0.1 to 100 parts by volume, more preferably 5 to 100 parts by volume of reagent 5 can be added with respect to 1 part by volume of the body fluid sample.

Furthermore, the present invention provides a kit for extracting low-molecular-weight proteins/peptides contained in a body fluid sample. The kit comprises reagent 1 containing urea and thiourea, reagent 2 containing a reducing agent, reagent 3 containing 90% or more of an organic solvent, and reagent 4 containing an organic solvent and an acid. The reagents used in the kit are the same as reagents 1 to 4 used in the method of the present invention described above.

Specifically, the kit of the present invention comprises reagent 1 having a urea concentration of 1 to 8 M and a thiourea concentration of 0.5 to 3 M, reagent 2 containing the reducing agent at the concentration described above, reagent 3 containing 90% or more, preferably 95% or more of an organic solvent selected from the group consisting of acetone, ethanol, methanol, 2-propanol, acetonitrile, and mixtures thereof, and reagent 4 containing 50 to 99% of an organic solvent selected from the group consisting of acetonitrile, methanol, ethanol, isopropanol, and mixtures thereof and an acid selected from the group consisting of hydrochloric acid, TFA, formic acid, acetic acid, and TCA.

Furthermore, the kit of the present invention comprises reagent 1 having a urea concentration of 3 to 8 M and a thiourea concentration of 1 to 3 M, reagent 2 containing the reducing agent in a concentration of 10 to 300 mM, reagent 3 containing acetone as the organic solvent in a concentration of 98% or more, and reagent 4 containing acetonitrile as the organic solvent in a concentration of 60 to 80%.

Furthermore, the present invention provides a kit for preparing an analysis sample of low-molecular-weight proteins/peptides contained in a body fluid sample, the kit comprising reagents 1 to 4 and reagent 5, i.e., reagent 5 containing a component, reagent 5 being added to the lyophilized product of the extracted low-molecular-weight proteins, etc., and the component being selected from the group consisting of TFA, hydrochloric acid, formic acid, acetic acid, and TCA.

Next, the present invention will be described in detail and specifically with reference to Examples. The Examples below are intended to describe the present invention and do not limit the protection scope of the present invention by any means. A protective scope of the present invention is defined by the description of claims of the present application.

EXAMPLES

Example 1

Extraction of Low-Molecular-Weight Proteins, Etc

In the present example, the extraction of low-molecular-weight proteins, etc, according to the present invention was performed using human serum. FIG. 1 shows a flowchart of procedures of the present example. The "low-molecular-weight proteins, etc." described herein mean proteins/peptides having a molecular weight of 20,000 or less, and middle- to high-molecular-weight proteins that are not removed by the method of the present invention, and do not include most of high-molecular-weight major proteins such as albumin in serum.

In the present example, 20 μl of serum was used as a body fluid sample. To the serum, 36 μl of reagent 1 (7 M urea and 2 M thiourea) and 4° C. of reagent (200 mM DTT) were added and then mixed by vortexing. For this procedure, all of the serum, reagent 1, and reagent 2 were chilled to 4° C. and then used. Subsequently, the mixed solution was dropped into 1.8 ml of reagent 3 comprising highly pure acetone chilled to 4° C., mixed by vortexing immediately thereafter, and subsequently stirred in an atmosphere of 4° C. for 1 hour. After the stirring, the mixed solution was centrifuged (19,000×g) at 4° C. for 15 minutes using a refrigerated centrifuge, and the obtained supernatant was completely removed. To the residual precipitate, 400 μl of reagent 4 (70% acetonitrile, 12 mM hydrochloric acid, balance: water) at 4° C. was then added and stirred at 4° C. for 1 hour. Then, the mixed solution was centrifuged (19,000×g) at 4° C. for 15 minutes using a refrigerated centrifuge, and the obtained supernatant was recovered as an extracted solution of low-molecular-weight proteins, etc.

Subsequently, the extracted solution was lyophilized, and the obtained lyophilized product was dissolved by the addition of 80 μl of reagent 5 (99.9% $H_2O$ and 0.1% TFA).

In the same way as above, a mixture of 5 μl of serum and 4 μg of SPM, 10 μl of serum, and 5 μl of serum were separately treated to obtain samples for analysis. For these varying amounts of the treated serums, the amounts of the solvents 1 to 5 were changed to achieve the same ratio as that for the 20 μl of serum. For example, for 10 μl of serum, each amount of reagents 1 to 5 was 18 μl of reagent 1, 2 μl of reagent 2, 0.9 ml of reagent 3, 200 μl of reagent 4, and 80 μl of reagent 5.

Example 2

Evaluation of the Present Invention by Tricine-SDS-PAGE

The extracted solution obtained in example 1 was evaluated as a sample by separating the solution by electrophoresis for low molecular weights (Tricine-SDS-PAGE), followed by Coomassie staining.

Samples used are the extracted solution of serum obtained by the method of example 1, untreated serum, a standard peptide mixture (SPM), and a mixed solution of untreated serum and SPM. The SPM used here is a cyanogen bromide degradation product of horse heart globulin and is a mixture containing 6 peptide fragments of molecular weights 16,949, 14,404, 10,700, 8,159, 6,214, and 2,512. The SPM is a reagent (manufactured by GE Healthcare Bio Science) used as a molecular weight marker in electrophoresis.

Gel used in the Tricine-SDS-PAGE had composition described in Table 1 below.

TABLE 1

| Composition of Tricine-SDS-PAGE gel | |
|---|---|
| Resolving gel (lower layer) | |
| 1.5M Tris - HCl pH 8.45 | 3.3 ml |
| 48% acrylamide (3% bisacrylamide) | 3.3 ml |
| Glycerol | 1.0 ml |
| Distilled water | 2.4 ml |
| TEMED | 3.4 μl |
| 10% APS | 50 μl |
| Resolving gel (middle layer) | |
| 1.5M Tris - HCl pH 8.45 | 0.835 ml |
| 48% acrylamide (3% bisacrylamide) | 0.5 ml |
| Distilled water | 1.165 ml |
| TEMED | 1.0 μl |
| 10% APS | 12.5 μl |
| Extracting gel (upper layer) | |
| 1.5M Tris - HCl pH 8.45 | 1.24 ml |
| 48% acrylamide (3% bisacrylamide) | 0.4 ml |
| Distilled water | 3.36 ml |
| TEMED | 3.4 μl |
| 10% APS | 50 μl |

Moreover, the Tricine-SDS-PAGE was performed under conditions described in Reference document 7.

Subsequently, the gel containing the developed samples was taken and Coomassie-stained. The Coomassie staining was performed using the following reagents and method:
Reagent 1 (staining solution: 30% methanol, 10% acetic acid, 0.1% [w/v] Coomassie R-350, balance: water)
Reagent 2 (destaining solution: 30% methanol, 10% acetic acid, balance: water)

In the staining procedures, the gel was taken from the gel plate after electrophoresis and transferred to a clean container having a smooth surface. Subsequently, reagent 1 was added to the container to soak the gel in reagent 1, followed by shaking for 20 minutes. After the shaking, reagent 1 was removed. Then, reagent 2 was added thereto to soak the gel in reagent 2, followed by shaking until the background color became suitably light.

The obtained results are shown in FIG. 2. Lane (a) shows the result derived from 4 µg of SPM; lane (b) shows the result derived from 0.5 µl of untreated serum; lane (c) shows the result derived from a mixture of 5 µl of serum and 4 µg of SPM treated by the method of example 1; lane (d) shows the result derived from 5 µl of serum treated by the method of example 1; and lane (e) shows the result derived from 10 µl of serum treated by the method of example 1. The table above the electrophoresis pattern shows the amount of serum, the amount of SPM, and the presence or absence of the treatment of example 1.

Lane (d) shows that most of protein components were removed by virtue of the treatment by the method of the present invention, although lane (d) is derived from 5 µl of serum as an analyte, which is 10 times the volume of lane (b). Moreover, components of low-molecular-weight proteins, etc. were detected with higher intensity in lane (d) than in lane (b). In lane (e) showing the result from serum treated in a volume twice that of lane (d) by the method of the present invention, components of low-molecular-weight proteins, etc. were detected with intensity about twice that of lane (d). Lane (c) shows the result derived from the mixture of 4 µg of SPM (equal to the volume of lane (a)) and 5 µl of serum extracted in example 1. In the comparison of SPM bands between lanes (c) and (a), all the bands were detected with almost the same intensities. This could demonstrate that the method of the present invention has extraction efficiency of low-molecular-weight proteins, etc. close to almost 100%. As can be seen from these results, the method of the present invention could efficiently recover SPM and could extract low-molecular-weight proteins, etc. in serum with high efficiency. Moreover, components of low-molecular-weight proteins, etc. could be almost doubled in amount in the extract by doubling the amount of serum extracted, suggesting that the peptides in the sample can be extracted with their quantitative information maintained. Thus, the method of the present invention is shown to be a method capable of extracting low-molecular-weight proteins, etc. with high efficiency with their quantitative information maintained, without being influenced by carrier proteins.

Example 3

Evaluation of the Present Invention by Reverse-Phase HPLC

FIG. 3 shows the results of analyzing by reverse-phase HPLC the samples of low-molecular-weight proteins, etc. extracted by the method of example 1. Graph (A) shows the analysis result at retention times of 20 to 70 minutes, and graph (B) shows a 5× magnified view of chromatographic peak intensities at the retention times of 30 to 40 minutes in graph (A). Moreover, the black line in the chromatograph represents the analysis result of 0.5 µl of untreated serum, and the gray line in the chromatograph represents the analysis result of the sample obtained from 5 µl of serum treated by the method of example 1. In the reverse-phase HPLC, low-molecular-weight proteins, etc. tend to be extracted at earlier retention times (40 minutes or earlier), while high-molecular-weight proteins, etc. tend to be extracted at later retention times (40 minutes or later).

The gray line in the chromatograph shows the result of low-molecular-weight proteins, etc. extracted by the method of example 1 from 5 µl of serum that is 10 times the volume of the black line in the chromatograph. In the comparison between the gray and black lines in chromatograph (A), almost no peak is seen at retention times of 40 minutes or later in the gray line. This result demonstrates that most of high-molecular-weight major proteins, etc. such as albumin were removed. Moreover, in chromatograph (B), almost no detectable peak is observed in the black line, whereas many peaks can be detected in the gray line. This result demonstrates that low-molecular-weight proteins, etc. in serum were extracted.

Example 4

Confirmation of Reproducibility of Method of the Present Invention

To confirm the concentration reproducibility of the method of the present invention for low-molecular-weight proteins, etc., 10 µl each of identical serums was independently extracted 6 times according to the procedures of example 1, and the obtained extracts were respectively analyzed by Tricine-SDS-PAGE. The results are shown in FIG. 4. As can be seen from FIG. 4, the detected bands were confirmed to be identical in all the lanes, and the corresponding bands in the lanes were detected with almost the same intensities and thicknesses. This result could demonstrate that the method of the present invention can extract low-molecular-weight proteins, etc. with high reproducibility.

Example 5

Identification of Low-Molecular-Weight Proteins, etc. Extracted by Method of the Present Invention Low-molecular-weight proteins, etc. extracted by the method of example 1 were developed using Tricine-SDS-PAGE, and major peptides detectable as distinct bands and unremoved proteins were identified. The method and the results are shown below.
(Separation of Low-Molecular-Weight Proteins, Etc.)

First, an extracted solution obtained by treating 10 µl of serum as a sample by the method of example 1 was separated by Tricine-SDS-PAGE. After Coomassie staining, the bands to be identified were excised to obtain a plurality of gel pieces. The gel pieces were completely destained with a 50 mM ammonium bicarbonate solution containing 50% acetonitrile. The gel pieces were washed with distilled water, then dehydrated in 100% acetonitrile for 15 minutes, and dried in a centrifugal evaporator for 60 minutes. To the dried gel pieces, 10 to 30 µl of 0.5 ng/µl trypsin (Roche Diagnostics GmbH) dissolved in 25 mM Tris-HCl (pH 9.0) was added and absorbed into the gel pieces for 45 minutes in ice. Then, excess trypsin solutions were removed, and 50 mM Tris-HCl pH 9.0 was added thereto to soak the gel in the solution, followed by in-gel digestion at 37° C. for 18 hours. After the completion of the enzymatic digestion, the whole solution surrounding the gel pieces was recovered and temporarily stored in ice. To further recover peptide fragments still remaining in the gel, a 5% formic acid solution containing 50% acetonitrile was added thereto to soak the gel in the solution, and the mixture was stirred at room temperature for 20 minutes. After the stirring, the supernatant was added to the preceding solution stored in advance. The solution was subjected to measurement using an LC-MS* apparatus and database search using software for protein identification (SEQUEST SEARCH: Thermo Fisher Scientific Inc.).
*LC-MS: Liquid Chromatography-Mass Spectrometry
Liquid Chromatography Nanospace SI-2 (Shiseido Fin Chemicals)
Mass Spectrometry: LCQ-DECA (manufactured by Thermo Fisher Scientific Inc.)

(Analysis Results)

Bands of the separated low-molecular-weight proteins, etc. are shown in FIG. 5, and the identification results are shown in Table 2. FIG. 5 shows at the left the molecular weights of the low-molecular-weight proteins, etc. in the bands and at the right the band numbers of the identified proteins, etc. The band number in Table 2 corresponds to that in FIG. 5. In Table 2, the molecular weights represent those shown in the database for the identified proteins/peptides, and the names of proteins etc. represent the names of the identified proteins/peptides. As can be seen from the Tricine-SDS-PAGE results of FIG. 5, proteins having a molecular weight of 20,000 or higher and low-molecular-weight proteins, etc. having a molecular weight of 20,000 or lower were identified.

TABLE 2

Results of identifying peptides, etc in serum

| Band number | Molecular weight | Names, etc. of proteins, etc. |
|---|---|---|
| 1 | 77050 | Transferrin/transferrin precursor/serotransferrin precursor (transferrin) (siderophilin) (beta-1-metal-binding globulin) (PR01400) |
| 2 | 66472 | Chain A, human serum albumin complexed with S-(−) enantiomer of warfarin and myristic acid |
|  | 69226 | Serum albumin precursor |
|  | 69084 | Serum albumin |
| 3 | 46723 | Serine (or cysteine) proteinase inhibitor, clade A (alpha-1 anti-proteinase, anti-trypsin), member 1 |
|  | 46721 | PRO0684 |
| 4 | 66036 | Human serum albumin complexed with myristic acid and triiodobenzoic acid |
|  | 65221 | Chain A, crystal structure of GA module complexed with human serum albumin |
|  | 71705 | ALB protein |
| 5 | 45371 | Apolipoprotein A-IV precursor |
|  | 45399 | Apolipoprotein A-IV |
| 6 | 36154 | Preapolipoprotein E/apolipoprotein E precursor/apolipoprotein E |
| 7 | 30778 | Apolipoprotein A-I/apolipoprotein A-I precursor/preproapolipoprotein A-I/proapolipoprotein |
|  | 23404 | Chain D, crystal structure of human apolipoprotein A-I |
| 8 | 45205 | Haptoglobin/haptoglobin alpha (2FS)-beta precursor/haptoglobin precursor |
|  | 41525 | Hp2-alpha |
|  | 20820 | PREDICTED: analogous to haptoglobin precursor, allele |
| 9 | 15873 | TTR |
|  | 13761 | Chain D, monoclinic crystal structure of transthyretin complexed with diethylstilbestrol |
|  | 15771 | Chain D, deoxy |
|  | 15887 | Transthyretin (prealbumin, amyloidosis type I) |
| 10 | 45205 | Haptoglobin/haptoglobin alpha (2FS)-beta precursor/haptoglobin precursor |
|  | 41525 | Hp2-alpha |
|  | 23305 | Chain A, trypsin inhibitor complex |
|  | 15877 | Chain D, crystallographic analysis of interaction of quaternary-T human hemoglobin with nitric oxide, hemoglobin exposed to no under aerobic conditions |
|  | 14807 | Serum amyloid A4/serum amyloid A-4 protein precursor |
| 11 | 10852 | Apolipoprotein C-III/apolipoprotein C-III precursor/preapolipoprotein C-III/apolipoprotein |
|  | 47009 | Developmentally regulated protein TP01 |
|  | 11585 | Serum amyloid A protein beta des-Arg (pI 5.6) |
| 12 | 41525 | Hp2-alpha |
|  | 45205 | Haptoglobin/haptoglobin alpha (2FS)-beta precursor/haptoglobin precursor |
|  | 13894 | Pro-platelet basic protein precursor/platelet basic protein/leukocyte-derived growth factor/connective tissue-activating peptide III/PPBP |
|  | 10852 | Apolipoprotein C-III/apolipoprotein C-III precursor/preapolipoprotein C-III/apolipoprotein |
| 13 | 8927 | Chain A, global structure and dynamics of human apolipoprotein C-II complexed with micelle |
|  | 11284 | Apolipoprotein C-II/apolipoprotein C-II precursor |
|  | 8915 | Chain A, structure of human apolipoprotein C-II in dodecylphosphocholine/chain A, NMR structure of human apolipoprotein C-II in presence of SDS |
| 14 | 11184 | Apolipoprotein |
|  | 27993 | Apolipoprotein D |
|  | 11288 | Apolipoprotein A-II |
| 15 | 6631 | Apolipoprotein C-1 |
|  | 11184 | Apolipoprotein |
|  | 27993 | Apolipoprotein D |

As shown in Table 2, a plurality of actually identified proteins/peptides existed in each excised gel piece, although FIG. 5 shows them as one band. This result suggests that the obtained extract contains a large number of low-molecular-weight proteins, etc. Moreover, the band at number 11 in FIG. 5 is supposed to indicate a molecular weight of approximately 11,000 estimated from the molecular weight at the right. However, a plurality of proteins identified at this band number included a protein having a molecular weight of 47,000 evidently larger than the estimated molecular weight. This indicates that a cleaved protein fragment was identified. This result indicates that most of the bands in the range of low-molecular-weight proteins, etc. contain a cleaved protein fragment. The protein fragment includes those released into blood flow due to cellular necrosis or apoptosis (Reference document 2). Therefore, the protein fragment may reflect various pieces of in-vivo information.

The band at number 2 in FIG. 5 was confirmed to be approximately 2 μg from the band intensity and contained albumin as the identified protein. The albumin is found in an amount of approximately 600 μg per 10 μl of serum in healthy people (Reference document 2). This result showed that approximately 99.7% albumin as the typical protein was removed. Moreover, apolipoprotein C-II at band number 13 in the region of low-molecular-weight proteins, etc. in Table 2 is found only in an amount of approximately 0.3 μg per 10 μl of serum in healthy people (Reference document 3). Thus, the apolipoprotein C-II is not the main component of serum (see FIG. 1). In the comparison of concentrations between albumin and apolipoprotein C-II in the serum, the albumin exists at a concentration about 2,000 times that of the apolipoprotein C-II. As a result of concentration using the method of the present invention, albumin and apolipoprotein C-II differing in concentration by about 2,000 times could be detected simultaneously by electrophoresis. This indicates that the majority of albumins were removed, while apolipoprotein C-II was efficiently extracted.

Comparative Example 1

Comparison with Conventional Method (Acetone Precipitation Method)

The method of the present invention was evaluated for its protein removal efficiency and peptide extraction efficiency by comparison with (1) acetone precipitation and (2) ultrafiltration methods as conventional general peptide extraction methods (Extraction methods).
(Acetone Precipitation Method)

In the acetone precipitation method, hydration water on the surface of protein molecules is lost due to the solvation of acetone, resulting in reduced solubility of the proteins and precipitation through the binding between the proteins. Proteins form a stable three-dimensional structure through hydration with solvents and are therefore precipitated easily using a high concentration of an organic solvent. By contrast, peptides are generally in a form dissolved without three-dimensional structure and are therefore hardly precipitated. The acetone precipitation method is a method by which only peptides are extracted as soluble fractions by use of this difference in solubility in the presence of the organic solvent. Thus, when serum is dropped into an acetone solvent, proteins are precipitated. Therefore, only peptides can be recovered as soluble fractions.
(Procedures of Acetone Precipitation Method)

In the present comparative example, the acetone precipitation method was performed with reference to the method of Matsuo or Chertov et al. (Reference Documents 4 and 5). FIG. 6 shows a flowchart of the acetone precipitation method.

SPM-mixed serum and unmixed serum were used as samples for evaluating peptide extraction efficiency. First, the serum was diluted by mixing the serum and 7 M urea/2 M thiourea at a ratio of 1:1. The diluted serum (10 μl) was slowly dropped into 90 μl of 75% acetone chilled to 4° C., and the mixture was stirred at 4° C. for 1 hour. Then, soluble fractions were recovered by centrifugation at 19,000×g at 4° C. for 15 minutes and lyophilized. The lyophilized product was dissolved in 20 μl of a sample buffer for PAGE and analyzed by Tricine-SDS-PAGE. The composition of the sample buffer for PAGE was 50 mM Tris-HCl (pH 6.8), 50 mM DTT, 0.5% SDS, and 10% glycerol.

The dilution of the serum with 7 M urea/2 M thiourea denatures proteins contained therein. This also inactivates protease and can therefore reduce its influence (Reference document 5). Moreover, recovery of carrier protein-bound peptides was judged as being possible, because the carrier proteins were also denatured.
(Results and Evaluation)

FIG. 7 shows the results of separating by Tricine-SDS-PAGE the peptides extracted from serum by the acetone precipitation method, followed by Coomassie staining. Lane (a) shows the analysis result derived from 8 μg of SPM; lane (b) shows the analysis result derived from 0.5 μl of untreated serum; lane (c) shows the analysis result derived from a mixture of 5 μl of serum and 8 μg of SPM treated by the acetone precipitation method; lane (d) shows the analysis result derived from 5 μl of serum treated by the acetone precipitation method; and lane (e) shows the analysis result derived from 8 μg of SPM treated by the acetone precipitation method. The table above the electrophoresis pattern shows the amount of serum, the amount of SPM, and the presence or absence of the treatment of the acetone precipitation method.

Lane (d) shows that most of proteins (molecular weight: 20,000 or higher) were removed by virtue of the treatment by the acetone precipitation method, although lane (d) shows the analysis result derived from 5 μl of serum that is 10 times the volume of lane (b). It is further shown that peptide components (molecular weight: 20,000 or less) were extracted because these peptide components were detected with higher intensity in lane (d) than in lane (b). On the other hand, two bands observed in the molecular weight range of 14,000 to 17,000 in lane (b) were lost in lane (d) due to the acetone precipitation. Moreover, lanes (a), (c), and (e) contained the same amounts (8 μg) of SPM. Only the sample of lane (c) was supplemented with 5 μl of serum. Lane (e) showing the result from only SPM treated by the acetone precipitation method demonstrated that all the SPM components were efficiently recovered. However, in lane (c) showing the result from serum supplemented with SPM, the components other than those of the molecular weight of 6,000 in SPM were lost due to the acetone precipitation method and were not detected. This suggests that SPM was bound to carrier proteins and removed together therewith, in spite of the fact that the serum was diluted with 7 M urea/2 M thiourea.

As can be seen from FIG. 5, two major peptides (molecular weights: 14,000 and 17,000) in serum as well as SPM added in advance to serum were lost due to the peptide extraction using the acetone precipitation method, suggesting that carrier protein-bound peptides cannot be extracted by the acetone precipitation method. Specifically, the acetone precipitation method was shown to have the difficulty in extracting peptides present in serum with their quantitative information maintained.

Comparative Example 2

Comparison with Conventional Method (Ultrafiltration Method)

The ultrafiltration method is a method by which peptides are extracted using an ultrafiltration membrane that permits molecules equal to or smaller than a particular size to pass therethrough but not larger molecules. When serum is filtered through the ultrafiltration membrane, ideally, proteins are extracted without passing through the filtration membrane while only peptides pass therethrough. Thus, only peptide components can be separated as a filtrate. The ultrafiltration method is a convenient, high-throughput method and is therefore used most frequently in peptide extraction from serum and plasma.

(Procedures of Ultrafiltration Method)

In the present comparative example, the ultrafiltration method was performed with reference to the method of Tirumalai et al. or Harper et al. (Reference documents 2 and 6). FIG. 8 shows a flowchart of the ultrafiltration method.

The ultrafiltration membrane was used after washing. The washing was performed by placing 25 mM ammonium bicarbonate/20% acetonitrile onto the ultrafiltration membrane (MICROCON YM-30, manufactured by Millipore Corporation; molecular cutoff: 30,000) and gently stirring the mixture, followed by centrifugation at 3,000×g for 5 minutes and subsequent removal of the filtrate.

SPM-mixed serum and unmixed serum were used as samples for evaluating peptide extraction efficiency. The serum was diluted by mixing the serum and 25 mM ammonium bicarbonate/20% acetonitrile at a ratio of 1:5. The diluted serum was placed on the thus-washed ultrafiltration membrane and centrifuged at 3,000×g at 4° C. for 15 minutes. The obtained filtrate was recovered and lyophilized. The lyophilized product was dissolved in 20 µl of a sample buffer for PAGE and analyzed by Tricine-SDS-PAGE. The composition of the sample buffer for PAGE was 50 mM Tris-HCl (pH 6.8), 50 mM DTT, 0.5% SDS, and 10% glycerol. The dilution of the serum with 25 mM ammonium bicarbonate/20% acetonitrile is performed for the purpose of reducing the viscosity of the serum and reducing adsorption of peptides to the filtration membrane (Reference document 6).

(Results and Evaluation)

FIG. 9 shows the results of analyzing by Tricine-SDS-PAGE the peptides extracted from serum by the ultrafiltration method. FIG. 9(A) shows Coomassie staining results, and FIG. 9(B) shows silver staining results. The silver staining has sensitivity 20 to 30 times that of the Coomassie staining. Lanes (A1) and (B1) respectively show the analysis result derived from 4 µg of SPM; lanes (A2) and (B2) respectively show the analysis result derived from 0.5 µl of untreated serum; lane (A3) shows the analysis result derived from a mixture of 5 µl of serum and 4 µg of SPM treated by the ultrafiltration method; lanes (A4) and (B3) respectively show the analysis result derived from 5 µl of serum treated by the ultrafiltration method; lanes (A5) and (B4) respectively show the analysis result derived from 10 µl of serum treated by the ultrafiltration method; and lanes (A6) and (B5) respectively show the analysis result derived from 100 µl of serum treated by the ultrafiltration method. The table above the electrophoresis pattern shows the amount of serum, the amount of SPM, and the presence or absence of the treatment of the ultrafiltration method.

(A) Evaluation Based on Coomassie Staining

Lane (A3) shows the result derived from the mixture of 4 µg of SPM (equal to the volume of lane (A1)) and 5 µl of serum (10 times the volume of lane (A2)) treated by ultrafiltration. It is shown that proteins and also SPM were completely removed because both of them were not detected. Moreover, lanes (A4), (A5), and (A6) show the results obtained from 5 µl, 10 µl and 100 µl of serums, respectively, treated by the ultrafiltration method. In all of these lanes (A4), (A5), and (A6), both proteins and peptides were not detected. These results demonstrated that the ultrafiltration method has very high protein removal efficiency but very poor peptide extraction efficiency.

(B) Evaluation Based on Silver Staining

Lanes (B3), (B4), and (B5) show the results obtained from 5 µl, 10 µl, and 100 µl of serums, respectively, treated by the ultrafiltration method. Peptides were detected only in the 100 µl of treated serum in lane (B5). From the comparison between lane (B5) and lane (B2) (0.5 µl of untreated serum), it is shown that the proteins were completely removed in lane (B5). Moreover, in the comparison of peptide components therebetween, more bands were detected in lane (B2) that is 1/200 of the serum volume of lane (B5), demonstrating that the ultrafiltration method has peptide extraction efficiency of 0.5% or lower.

The results of (A) and (B) demonstrated that the ultrafiltration method can completely remove proteins but has peptide extraction efficiency as very poor as 0.5% or lower.

Proteins have previously been known to be lost due to their adsorption to an ultrafiltration membrane. Thus, the possible cause of the poor peptide extraction efficiency of the ultrafiltration method is that the majority of peptides cannot pass through the filtration membrane due to the peptide adsorption to the filtration membrane and the concentration of carrier protein-bound peptides together with the carrier proteins on the membrane.

Discussion (Comparison of Method of the Present Invention, Acetone Precipitation Method, and Ultrafiltration Method)

Peptides were extracted from mixtures of serum and SPM and then analyzed by Tricine-SDS PAGE to examine the protein removal efficiency of the peptide extraction methods and to evaluate their peptide extraction efficiency based on the amount of SPM remaining. In both the conventional acetone precipitation and ultrafiltration methods, the majority of SPM components were lost with the single exception of the peptide of the molecular weight 6,000 in SPM that was extracted by the acetone precipitation method, although these conventional methods had high protein removal efficiency. The possible reason for the lost SPM is that in the acetone precipitation method, carrier protein-adsorbed peptides cannot be recovered and that in the ultrafiltration method, the majority of the peptides were lost due to the filtration membrane in addition to this impossible recovery.

To solve these problems, the method of the present invention was developed and evaluated for its protein removal efficiency and peptide extraction efficiency using (1) Tricine-SDS-PAGE and (2) reverse-phase HPLC. Moreover, the method of the present invention was evaluated for its reproducibility using (3) Tricine-SDS-PAGE. Furthermore, (4) identification of major peptides extracted by the method of the present invention was carried out. As can be seen from the results of (1) Tricine-SDS-PAGE, the method of the present invention has high protein removal efficiency and could recover all the SPM components unrecoverable by the conventional methods. This demonstrated that the method of the present invention can extract peptides with high efficiency without being influenced by carrier proteins. The results of (2) reverse-phase HPLC could also demonstrate that the method of the present invention has high protein removal efficiency and can detect many peptide peaks and efficiently extract peptides. Moreover, the results of (3) Tricine-SDS-PAGE demonstrated that the method of the present invention can extract peptides with high reproducibility. Furthermore, the results of (4) identification of major peptides extracted by the method of the present invention demonstrated that even in terms of only major components, many peptides exist in the extract obtained by the method of the present invention and the extract includes protein fragments having various pieces of in-vivo information. It was further demonstrated that the method of the present invention can remove 99.7% albumin, the main protein component of serum, and can efficiently extract apolipoprotein C-II that exists in only 1/2000 of the volume of albumin in serum. Since the present method utilizes organic solvents and an acid, there was concern that proteins were cleaved by the present method to artificially form their fragments. However, this possibility is absent because SPM can be extracted with very high efficiency. Moreover, the possible influence of hydrochloric acid in reagent 4 was also eliminated because cleavage was not observed even at a hydrochloric acid concentration of 120 mM.

These results indicate that, according to the present invention, a method was obtained, which has high protein removal efficiency and can extract peptides (including carrier protein-adsorbed peptides) with high efficiency and good reproducibility with their quantitative information maintained.

These results are summarized in FIG. 10. As can be seen from the comparison among the lanes 3, 8, and 13, even SPM was efficiently recovered by the method of the present invention. By contrast, SPM was hardly recovered by the acetone precipitation (A) and ultrafiltration (F) methods. Moreover, carrier protein-adsorbed SPM in serum was probably removed together with the carrier proteins by the acetone precipitation and ultrafiltration methods. It is also shown that the largest number of serum-derived peptides other than SPM were extracted in the method of the present invention. Moreover, as can be seen from the comparison among the lanes 4, 9, and 14, the method of the present invention has a much higher serum-derived peptide recovery rate than that of the acetone precipitation or ultrafiltration method.

(Reference Documents)

[1] Fukutomi et. al. "A simple method for peptide purification as a basis for peptidome analysis", (J. Electrophoresis 49:15, 2005)

[2] Tirumalai R S, Chan K C, Prieto D A, Issaq H J, Conrads T P, Veenstra T D. "Characterization of the Low Molecular Weight Human Serum Proteome." (Mol. Cell. Proteomics 2003; 2:1096-103)

[3] Koga S, Japanese Journal of Clinical Medicine, 53, extra issue, 654, 1995

[4] Matsuo T and Nishi N, Lecture on New Chemical Experiments, 1, Protein I Separation/Purification/Properties, Chapter 3 Extraction Methods for Unconventional Proteins and Chapter 7 Fractional Precipitation

[5] Chertov O, Biragyn A, Kwak L W, Simpson J T, Boronina T, Hoang V M, Prieto D A, Conrads T P, Veenstra T D, Fisher R T. "Organic solvent extraction of proteins and peptides from serum as an effective sample preparation for detection and identification of biomarkers by mass spectrometry." (Proteomics 2004; 4: 1195-203)

[6] Harper R G, Workman S R, Schuetzner S, Timperman A T, Sutton J N. "Low-molecular-weight human serum proteome using ultrafiltration, isoelectric focusing, and mass spectrometry." (Electrophoresis 2004; 25:1299-306)

[7] Schagger H, von Jagow, G. "Tricine-sodium dodecyl sulfate-polyacrylamide gel electrophoresis for the separation of proteins in the range from 1 to 100 kDa". (Anal. Biochem. 1987; 166: 368-379)

INDUSTRIAL APPLICABILITY

A method of the present invention can efficiently extract carrier protein-bound low-molecular-weight proteins/peptides which are difficult to be extracted. Thus, the method of the present invention allows low-molecular-weight proteins, etc. in a liquid sample, particularly, in serum or plasma, to be analyzed by various chromatograph techniques, mass spectrometry, electrophoresis, NMR, ESR, various spectroscopy techniques, and the like. Specifically, the method of the present invention can be applied in a wide range to the medical fields such as diagnosis, diagnostic marker screening and drug development targeted for low-molecular-weight proteins, etc. in serum or plasma or the like. Moreover, the method of the present invention can be easily automated and thus allows an automated analyzer to be developed for low-molecular-weight proteins, etc. in blood.

BRIEF DESCRIPTION OF THE DRAWINGS

FIG. 10 shows the results of comparing the effects of the method of the present invention, the acetone precipitation method, and the ultrafiltration method based on Tricine-SDS-PAGE results.

Figure 1:
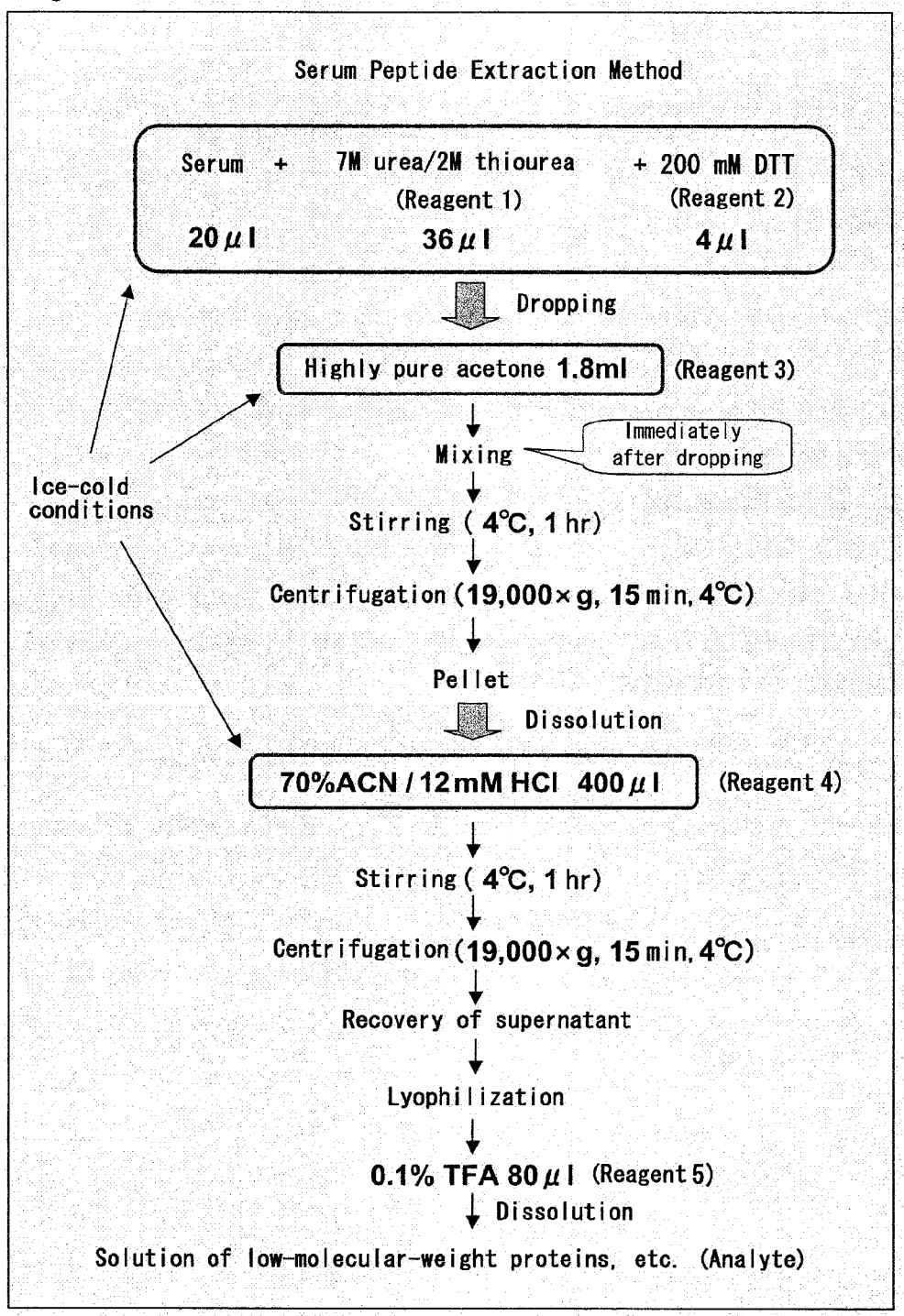
FIG. 1 is a flowchart showing procedures of performing example 1.
Figure 2:
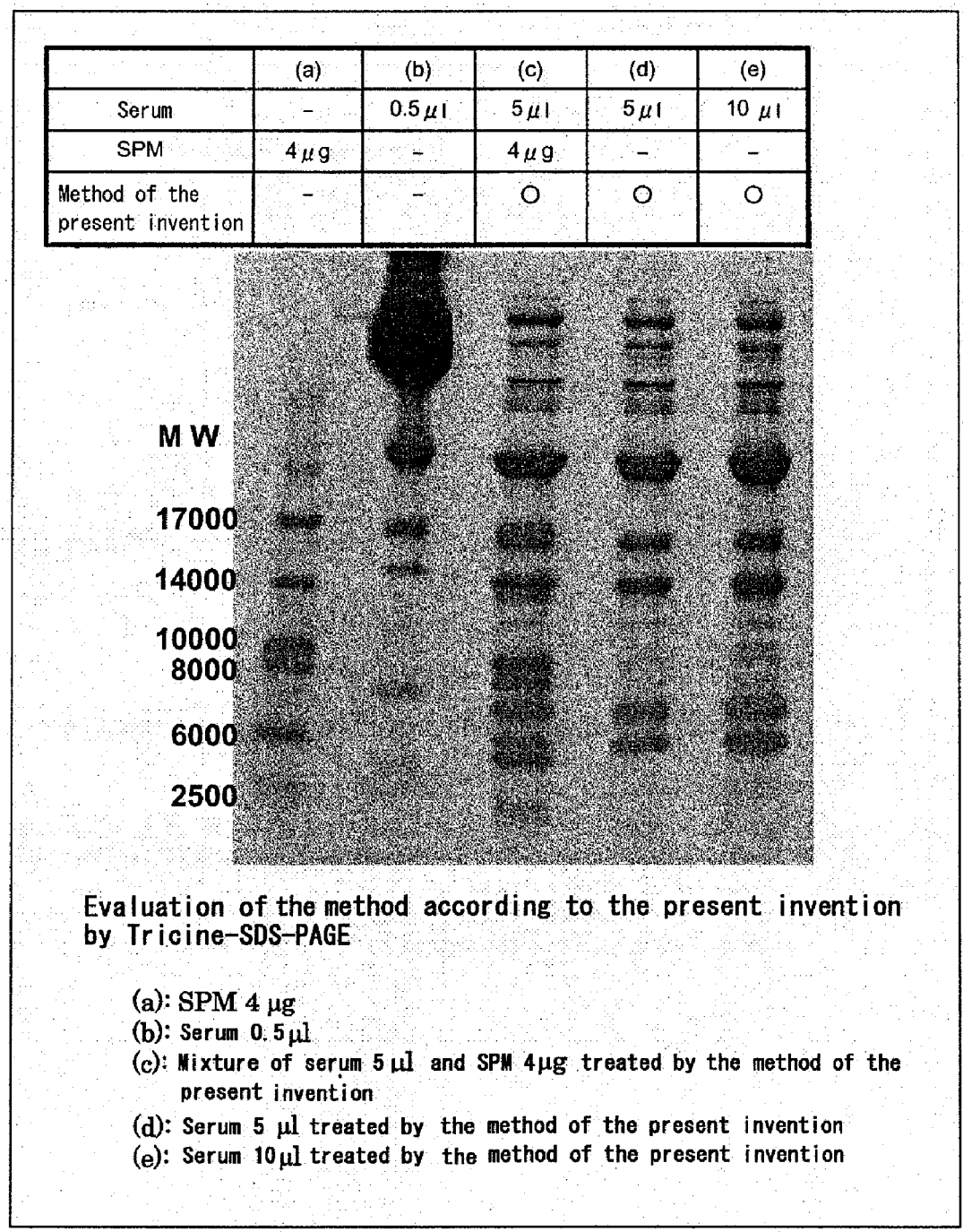
FIG. 2 is a photograph showing the results of separating by Tricine-SDS-PAGE an extracted solution obtained in example 1, followed by Coomassie staining.
Figure 3:
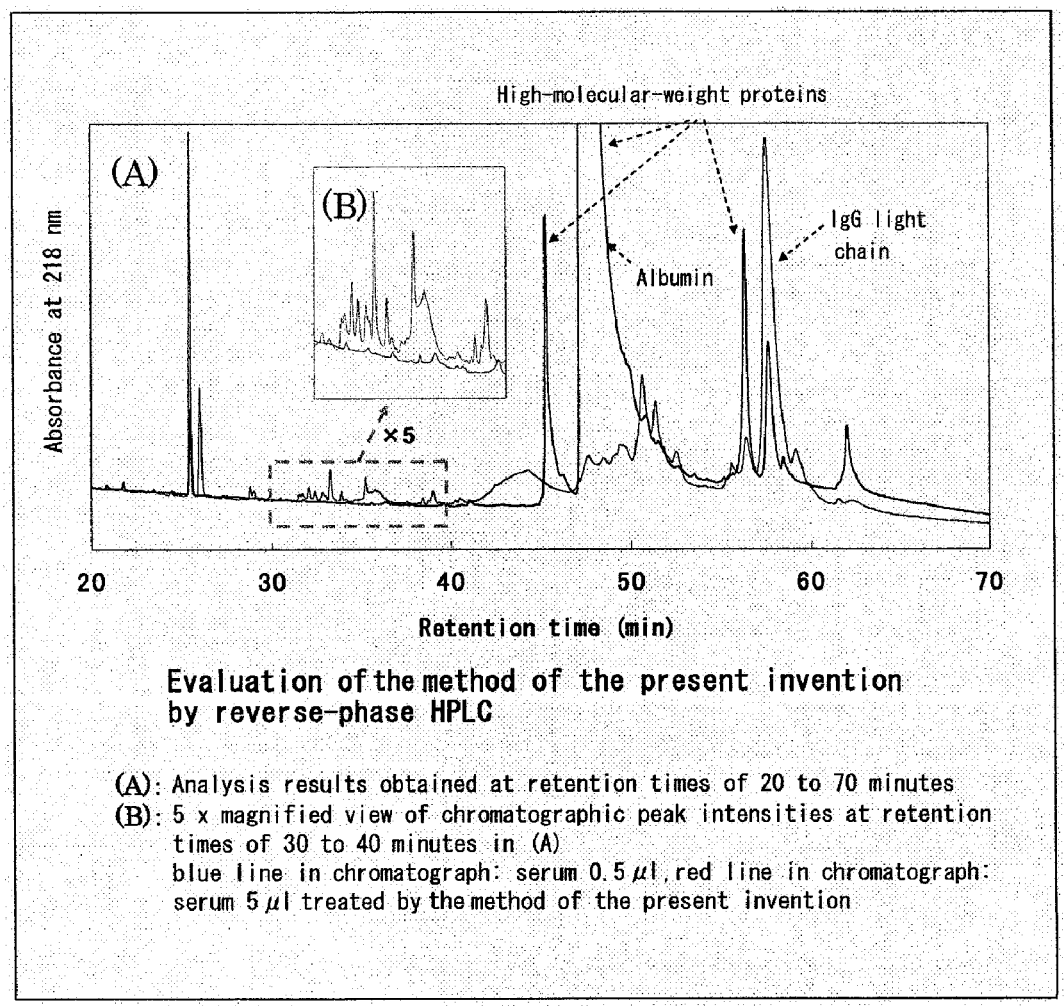
FIG. 3 is data showing the results of analyzing by reverse-phase HPLC a sample extracted by the method of example 1.
Figure 4:
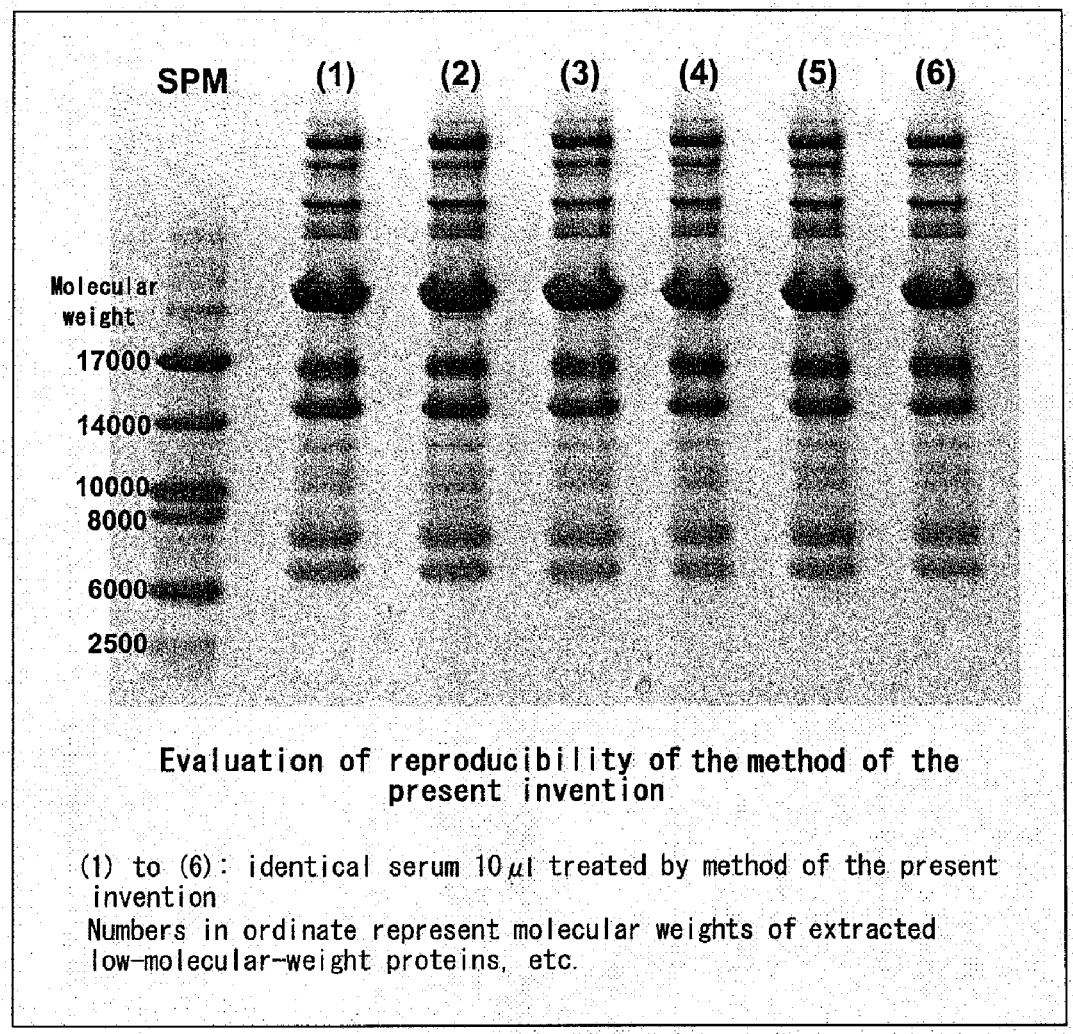
FIG. 4 is a photograph showing Tricine-SDS-PAGE results showing the extraction reproducibility of the method of the present invention.
Figure 5:
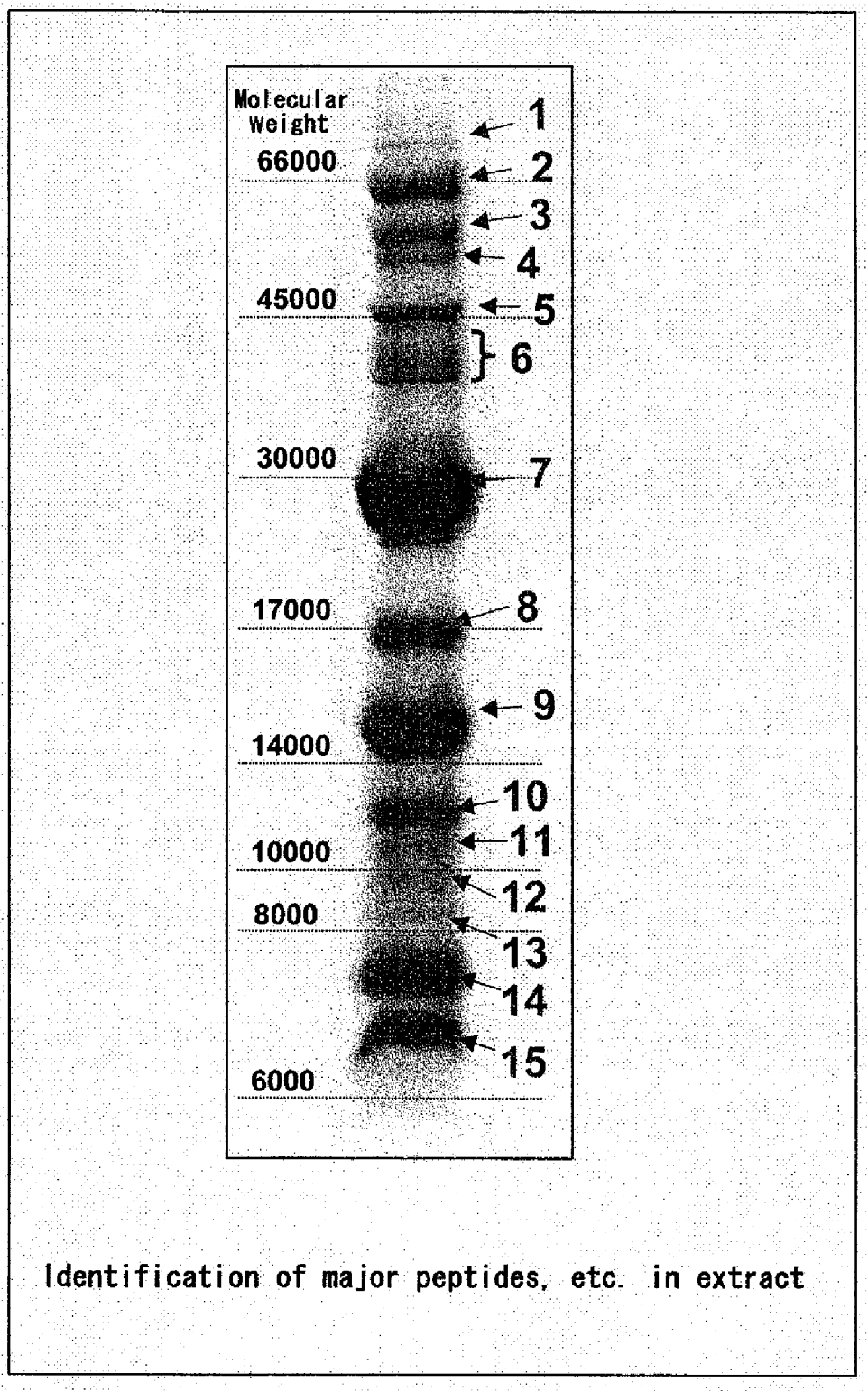
FIG. 5 is a photograph showing the results of separating by Tricine-SDS-PAGE an extracted solution obtained by the treatment of sample serum by the method of example 1, followed by Coomassie staining. Peptides, etc. were identified in each band.
Figure 6:
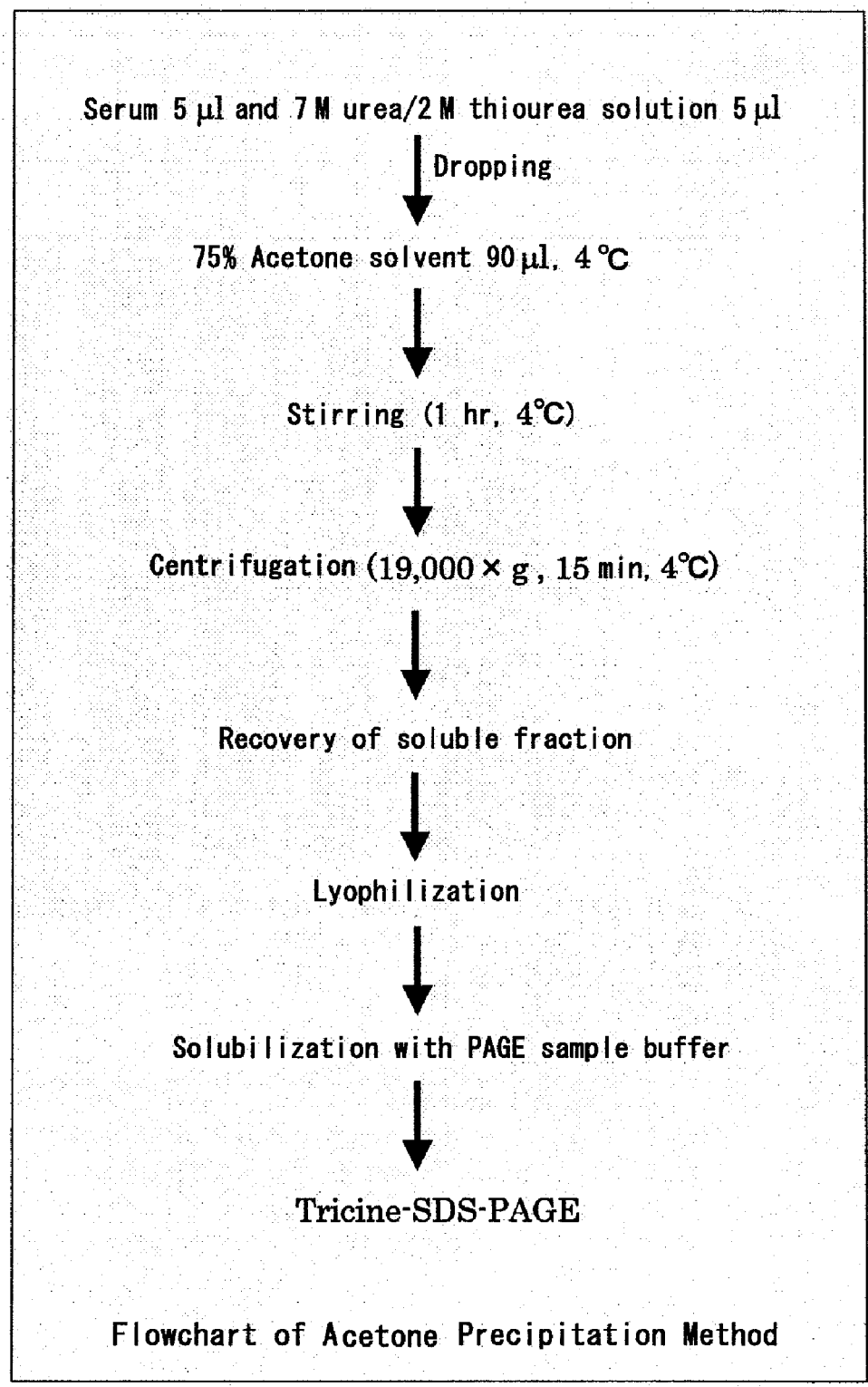
FIG. 6 shows a flowchart of an acetone precipitation method performed in comparative example 1.
Figure 7:
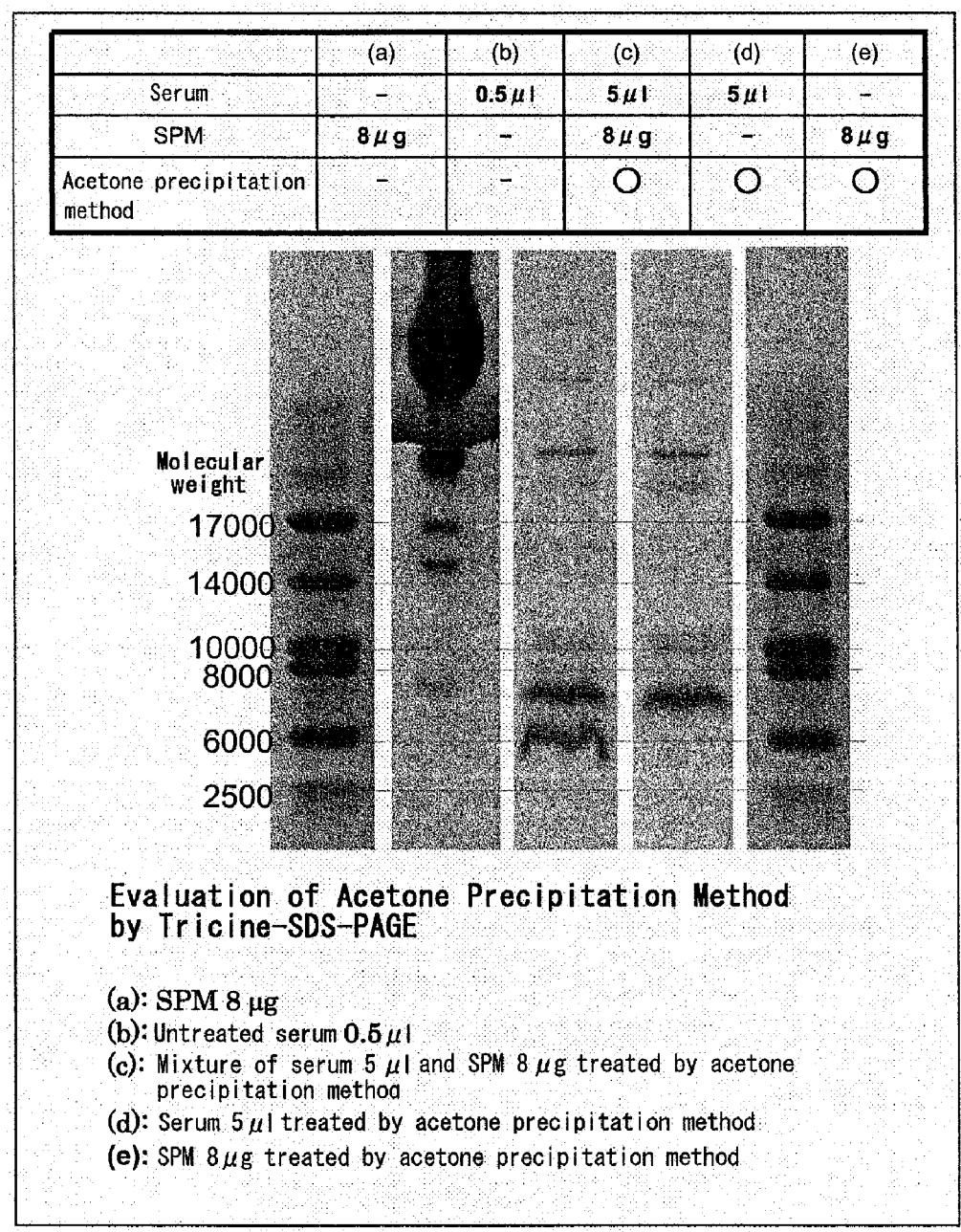
FIG. 7 is a photograph showing the results of Tricine-SDS-PAGE-separated peptides extracted from serum by the acetone precipitation method, followed by Coomassie staining.
Figure 8:
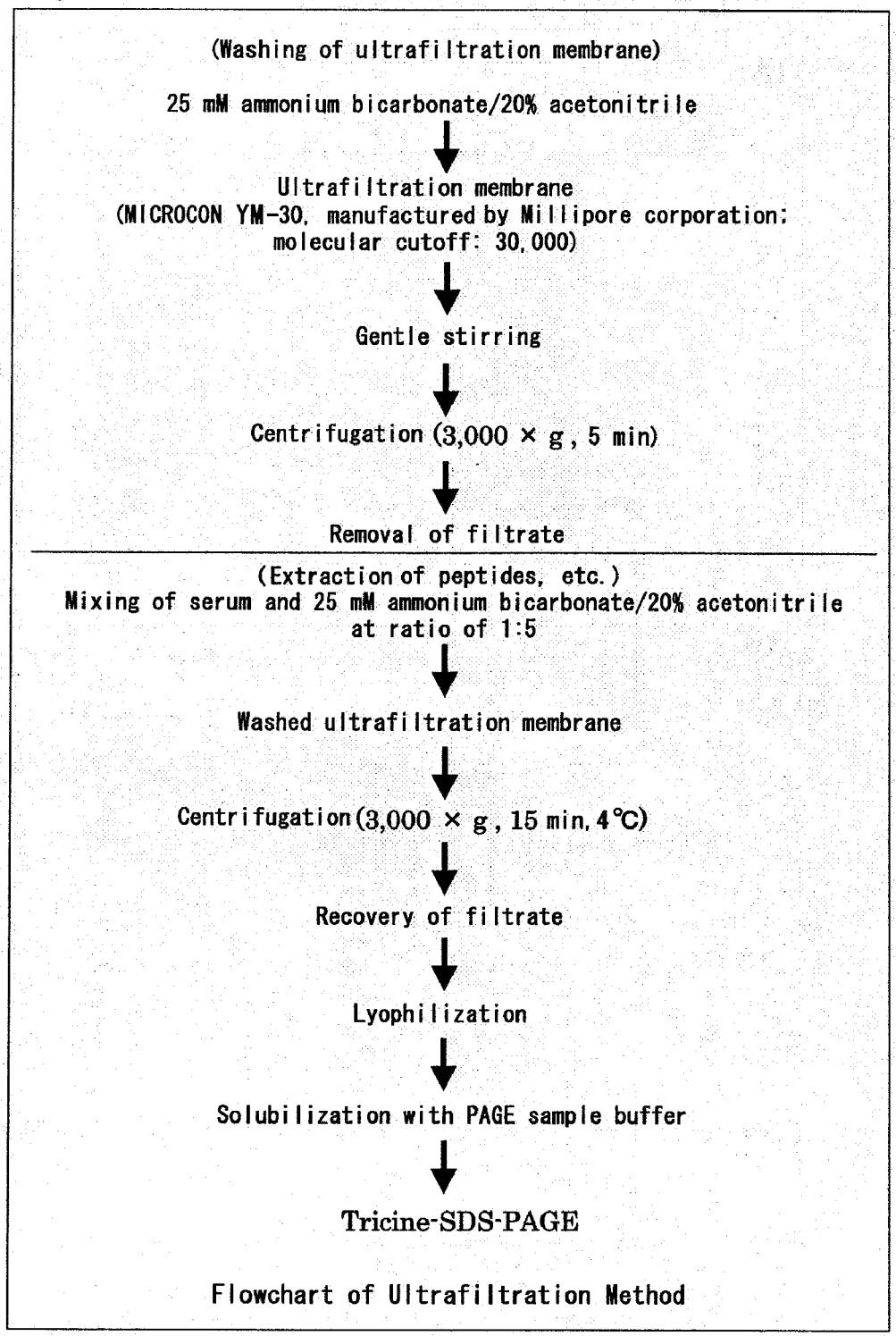
FIG. 8 shows a flowchart of an ultrafiltration method performed in comparative example 2.
Figure 9:
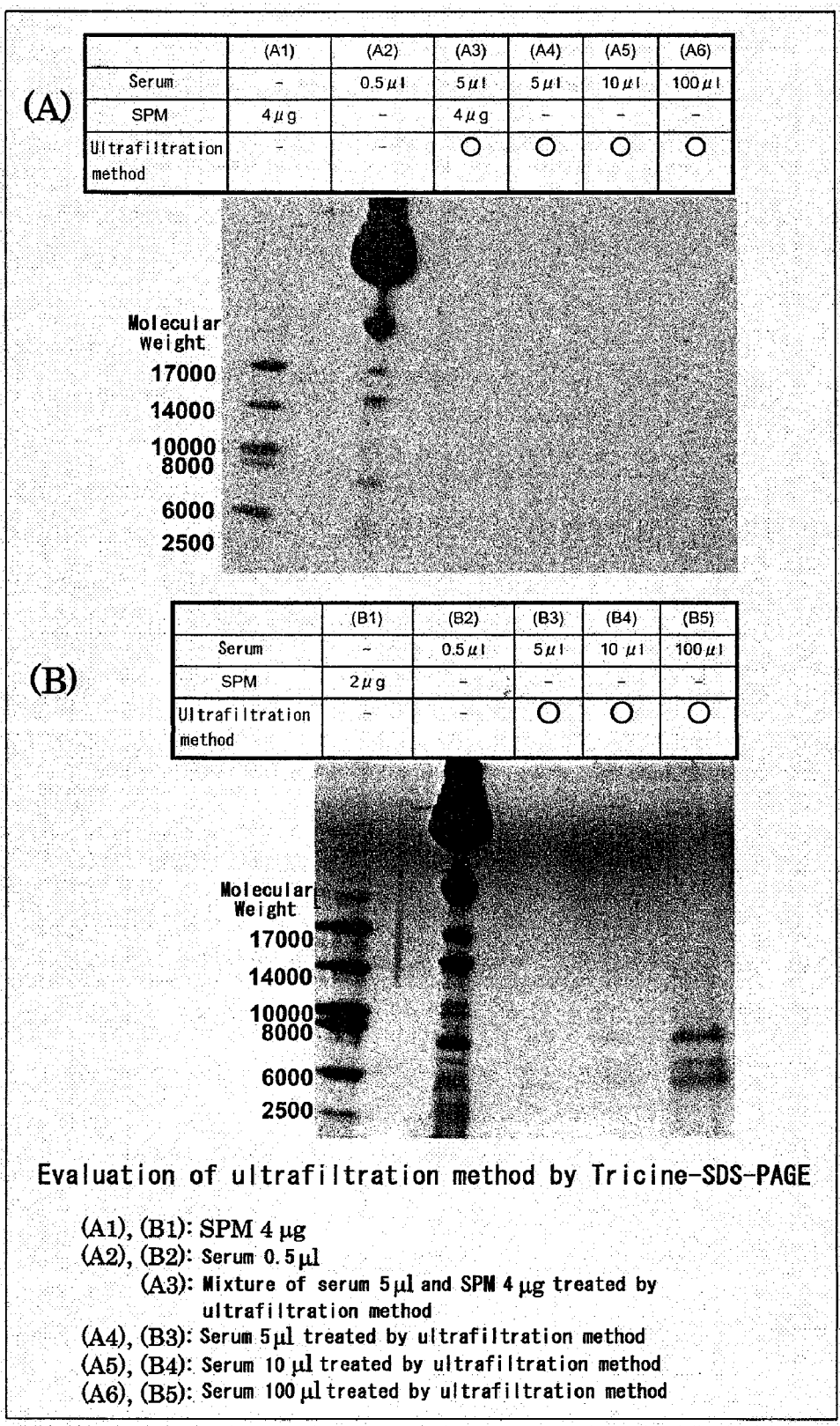
FIG. 9 is a photograph showing the results of Tricine-SDS-PAGE-separated peptides extracted from serum by the ultrafiltration method, followed by Coomassie staining.

The invention claimed is:

1. A method for extracting low-molecular-weight proteins/peptides contained in a body fluid sample, the method comprising the steps of:

(a) adding reagent 1 containing urea and thiourea and reagent 2 containing a reducing agent to the body fluid sample, mixing reagent 1, reagent 2 and the body fluid sample to form mixture 1, subsequently dropping the mixture 1 into reagent 3 containing 95% or more of an organic solvent, and mixing the mixture 1 and reagent 3 to form mixture 2, wherein a volume of reagent 3 used in the dropping is 20 times or more of the mixture 1;

(b) stirring at a temperature ranging from −20 to 10° C. the mixture 2 obtained in step (a);

(c) centrifuging at a temperature ranging from 0 to 10° C. the stirred solution obtained in step (b) and removing the supernatant;

(d) adding reagent 4 containing an organic solvent and an acid to the precipitate obtained in step (c) and mixing reagent 4 and the precipitate;

(e) stirring at a temperature ranging from −20 to 10° C. the mixed solution obtained in step (d); and (f) centrifuging at a temperature ranging from 0 to 10° C. the stirred solution obtained in step (e) and recovering the supernatant.

2. The method according to claim 1, further comprising the step of (g) lyophilizing the supernatant recovered in step (f).

3. The method according to claim 1, wherein the reducing agent in reagent 2 is selected from the group consisting of dithiothreitol (DTT), dithioerythritol (DTE), Triscarboxylphosphine (TCEP HCl), tributylphosphine (TBP), 2-mercaptoethanol (2-ME), 2-mercaptoethanolamine (2-MEA), and mixtures thereof.

4. The method according to claim 1, wherein the body fluid sample is serum or plasma.

5. The method according to claim 1, wherein reagent 1 has a urea concentration of 1 to 8 M and a thiourea concentration of 0.5 to 3 M, and reagent 2 contains the reducing agent in such an amount that the concentration of reducing agent in the mixture of the body fluid sample, reagent 1, and reagent 2 is 1 mM to 20 mM.

6. The method according to claim 5, wherein reagent 1 has a urea concentration of 3 to 8 M and a thiourea concentration of 1 to 3 M.

7. The method according to claim 5, wherein when the reducing agent in reagent 2 is dithiothreitol (DTT), dithioerythritol (DTE), 2-mercaptoethanol (2-ME), or 2-mercaptoethanolamine (2-MEA), reagent 2 contains the reducing agent in such an amount of concentration of the reducing agent in the mixture of the body fluid sample, reagent 1, and reagent 2 is 5 mM to 20 mM, or when the reducing agent is Tris(2-carboxyethyl)phosphine HCl (TCEP HCl) or tri-n-butylphosphine (TBP), reagent 2 contains the reducing agent in a concentration of 1 mM to 10 mM in the mixture of the body fluid sample, reagent 1 and reagent 2.

8. The method according to claim 1, wherein the organic solvent in reagent 3 is selected from the group consisting of acetone, ethanol, methanol, 2-propanol, acetonitrile, and mixtures thereof.

9. The method according to claim 8, wherein the organic solvent in reagent 3 is acetone.

10. The method according to claim 8, wherein reagent 3 contains the organic solvent in a concentration of 98% or more.

11. The method according to claim 1, wherein the organic solvent in reagent 4 is selected from the group consisting of acetonitrile, methanol, ethanol, isopropanol, and mixtures thereof and has a concentration of 50 to 99%, and the acid is selected from the group consisting of hydrochloric acid, trifluoroacetic acid (TFA), formic acid, acetic acid, and trichloroacetic acid (TCA).

12. The method according to claim 11, wherein the organic solvent in reagent 4 is acetonitrile.

13. The method according to claim 11, wherein the acid in reagent 4 is hydrochloric acid and has a concentration of 5 mM to 500 mM.

14. The method according to claim 11, wherein the organic solvent in reagent 4 has a concentration of 60 to 80%.

15. The method according to claim 11, wherein the organic solvent in reagent 4 has a concentration of 65 to 75%.

16. The method according to claim 1, wherein in step (b), the mixture 2 obtained in step (a) is stirred at a low temperature of −20° C. to 10° C. for 1 minute or more.

17. The method according to claim 16, wherein in step (b), the mixture 2 obtained in step (a) is stirred at a low temperature of 0° C. to 5° C. for 60 minutes or more.

18. The method according to claim 1, wherein in step (e), the mixed solution obtained in step (d) is stirred at a low temperature of −5° C. to 10° C. for 1 minute or more.

19. The method according to claim 18, wherein in step (e), the mixed solution obtained in step (d) is stirred at a low temperature of 0° C. to 5° C. for 60 minutes or more.

20. A method for preparing an analysis sample of low-molecular-weight proteins/peptides contained in a body fluid sample, which comprises providing a lyophilized product obtained by the method according to claim 2 and then adding reagent 5 containing a component to the lyophilized product to make the analysis sample, the component being selected from the group consisting of TFA, hydrochloric acid, formic acid, acetic acid, and TCA.

21. The method according to claim 20, wherein reagent 5 contains 0.1 to 20% TFA.

22. The method according to claim 20, wherein reagent 5 contains 0.1 to 20% formic acid, acetic acid, TCA, or mixtures thereof.

* * * * *